United States Patent [19]

Choi et al.

[11] Patent Number: 5,534,637

[45] Date of Patent: Jul. 9, 1996

[54] STARTING MATERIALS FOR PREPARTION OF SULFONYLUREA DERIVATIVES AND PROCESS FOR PREPARING THE SAME

[75] Inventors: Jong K. Choi; In B. Chung; Jae C. Lee; Byoung W. Suh; Jong S. Sa; Tae H. Heo, all of Daejeon, Rep. of Korea

[73] Assignee: Lucky Ltd., Seoul, Rep. of Korea

[21] Appl. No.: 350,979

[22] Filed: Nov. 29, 1994

Related U.S. Application Data

[62] Division of Ser. No. 205,400, Mar. 3, 1994, Pat. No. 5,480,993.

[30] Foreign Application Priority Data

| Mar. 5, 1993 | [KR] | Rep. of Korea | 93-3308 |
| Apr. 16, 1993 | [KR] | Rep. of Korea | 93-6409 |
| Oct. 7, 1993 | [KR] | Rep. of Korea | 93-20759 |

[51] Int. Cl.⁶ .................. C07D 231/14; C07D 231/16; C07D 231/28; C07D 231/30; C07D 231/54

[52] U.S. Cl. ............................................. 548/374.1

[58] Field of Search ................ 546/279; 548/551, 548/325.1, 378, 377, 374.1; 562/828

[56] References Cited

U.S. PATENT DOCUMENTS

| 4,546,179 | 10/1985 | Kunz | 544/206 |
| 4,762,550 | 8/1988 | Hartzell | 546/279 X |
| 4,954,164 | 9/1990 | Suzuki et al. | 544/298 X |
| 4,956,494 | 9/1990 | Husain et al. | 562/118 |
| 5,116,405 | 5/1992 | Makino et al. | 546/279 X |

FOREIGN PATENT DOCUMENTS

| 1445980 | 2/1969 | Germany | 546/279 |
| 1069040 | 5/1967 | United Kingdom | 546/279 |

*Primary Examiner*—Floyd D. Higel
*Attorney, Agent, or Firm*—Willian Brinks Hofer Gilson & Lione

[57] ABSTRACT

The present invention relates to a novel process for preparing sulfonylurea derivatives of formula (I) in a high purity and a high yield characterized in that a sulfonylchloride of formula (V) is reacted with 2-amino-4,6-dimethoxypyrimidine of formula (VII) in the presence of a metal cyanate and an organic base catalyst or a compound of formula (VIII) is reacted with 2-amino-4,6-dimethoxypyrimidine of formula (VII):

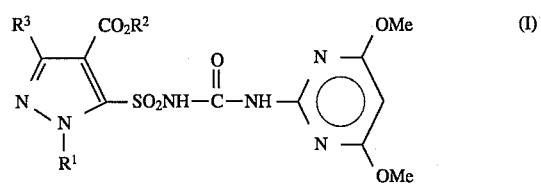

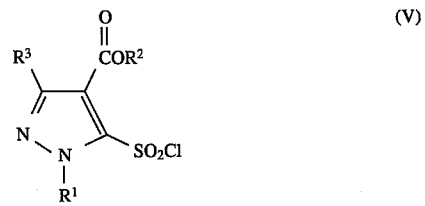

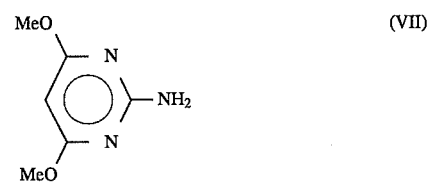

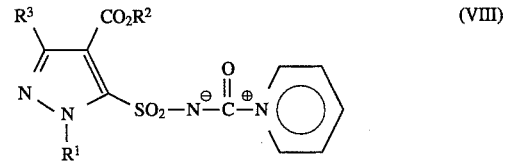

wherein $R^1$ represents hydrogen, $C_1$–$C_4$ alkyl or phenyl, $R^2$ represents hydrogen, $C_1$–$C_4$ alkyl, allyl or propargyl and $R^3$ represents hydrogen, methyl, ethyl or phenyl, and to a process for preparing the sulfonylchloride compound of formula (V) above and the compound of formula (VIII) above, both of which are useful as an intermediate compound for preparing the sulfonylurea derivative of formula (I) and to a novel intermediate compound of formula (VIII) as defined above.

6 Claims, No Drawings

STARTING MATERIALS FOR PREPARTION OF SULFONYLUREA DERIVATIVES AND PROCESS FOR PREPARING THE SAME

This is a divisional of application Ser. No. 08/205,400, filed Mar. 3, 1994 now U.S. Pat. No. 5,480,993.

BACKGROUND OF THE INVENTION

1. Field of Invention

The present invention relates to a novel process for preparation of sulfonylurea-based derivatives. Particularly, the present invention relates to a novel process for preparation of sulfonylurea derivatives having the following general formula (I),

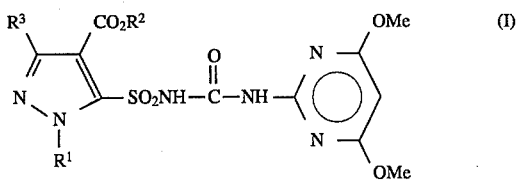

wherein $R^1$ represents hydrogen, $C_1$–$C_4$ alkyl or phenyl;

$R^2$ represents hydrogen, $C_1$–$C_4$ alkyl, allyl or propargyl; and $R^3$ represents hydrogen, methyl, ethyl or phenyl, and to an intermediate compound useful for this process and a process for preparing said intermediate compound.

2. Background Art

The sulfonylurea derivative of formula above is a known herbicide compound and processes for preparing the same are disclosed in numerous publications. For example, European Early Published Patent No. 87,780 discloses the three methods for preparing the compound (I), in which the first method comprises reacting an isocyanate of formula (II) with an amine compound of formula (VII); the second method comprises reacting an amine of formula (III) with an isocyanate of formula (VI); and the third method comprises reacting a carbamate of formula (IV) with an amine compound of formula (VII):

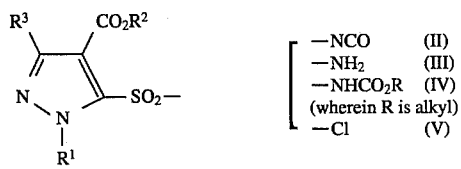

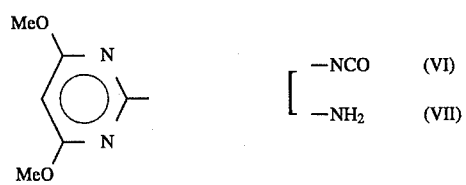

wherein $R^1$, $R^2$ and $R^3$ are as defined above.

Both the first and second methods as described above are the general methods for preparing sulfonylurea derivatives by synthesizing and separating isocyanates which are then reacted with amines. However, the isocyanate used as the starting material in these methods is synthesized by reacting the amine derivative of formula (III) or (VII) with a poisonous substance, phosgene. Accordingly, such methods using the isocyanate have some disadvantages in that mass use of phosgene in the industrial scale requires a special safety equipment, hydrochloric acid produced as by-product should be treated and the remaining phosgene should be recovered. Further, when the compound of formula (I) is prepared by reacting such isocyanate compound with the amine derivative, the yield of the desired product (I) is as low as 70 to 80%.

Moreover, as shown in the following reaction scheme, the first method produces the sulfonylurea derivative of formula (I) starting from the sulfonylchloride of formula (V) via the isocyanate of formula (II) according to a complicated multi-step procedure. Accordingly, this first method is disadvantageous in application to the mass production in the industrial scale.

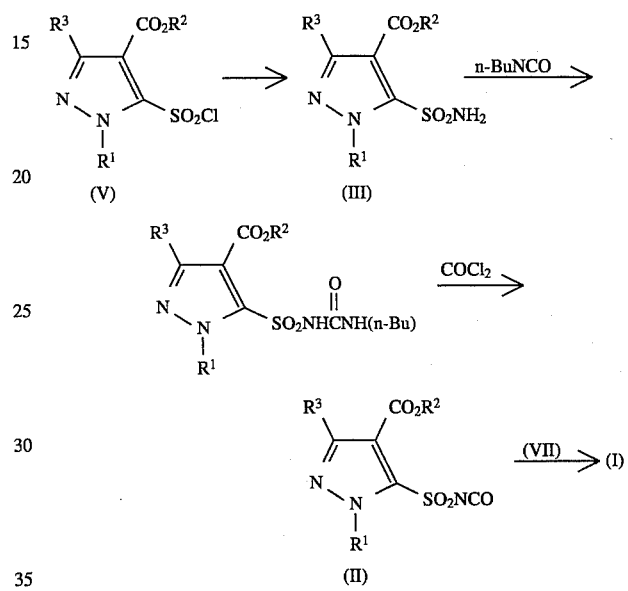

In addition, the third method as described above is a method identical to the method described in Japanese Laying-open Patent Publication No. (Hei) 03-200742 which requires a stringent reaction condition including high reaction temperature and produces the desired product (I) in a low yield. Therefore, this method is also unsuitable to the industrial scale production.

Thus, the present inventors have extensively studied to find out a method which can conveniently prepare the desired compound of formula (I) in a simple manner. As a result we have identified a novel single-step method capable of preparing the desired compound (I) in a high purity and in a high yield.

Therefore, it is an object of the present invention to provide a novel process for preparing the sulfonylurea derivative having the general formula (I) as defined above.

It is a further object of the present invention to provide a novel process for preparing an intermediate sulfonylchloride compound having the general formula (V) as defined above.

It is another object of the present invention to provide a novel intermediate compound having the general formula (VIII), as defined below, which can be used in the process for preparing the desired compound (I) according to the present invention.

Further, it is still another object of the present invention to provide a process for preparing the novel intermediate compound of formula (VIII).

The more pertinent and important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

DISCLOSURE OF INVENTION

In one aspect, the present invention relates to a novel process for preparing the desired sulfonylurea derivative of formula (I). Specifically, the present invention is to provide a process for preparing the desired compound of formula (I) which comprises reacting sulfonylchloride of formula (V) with 2-amino-4,6-dimethoxypyrimidine in the presence of a metal cyanate and an organic base catalyst as depicted in the following reaction scheme (A) or reacting a compound of formula (VIII) with 2-amino-4,6-dimethoxypyrimidine of formula (VII) as depicted in the following reaction scheme (B).

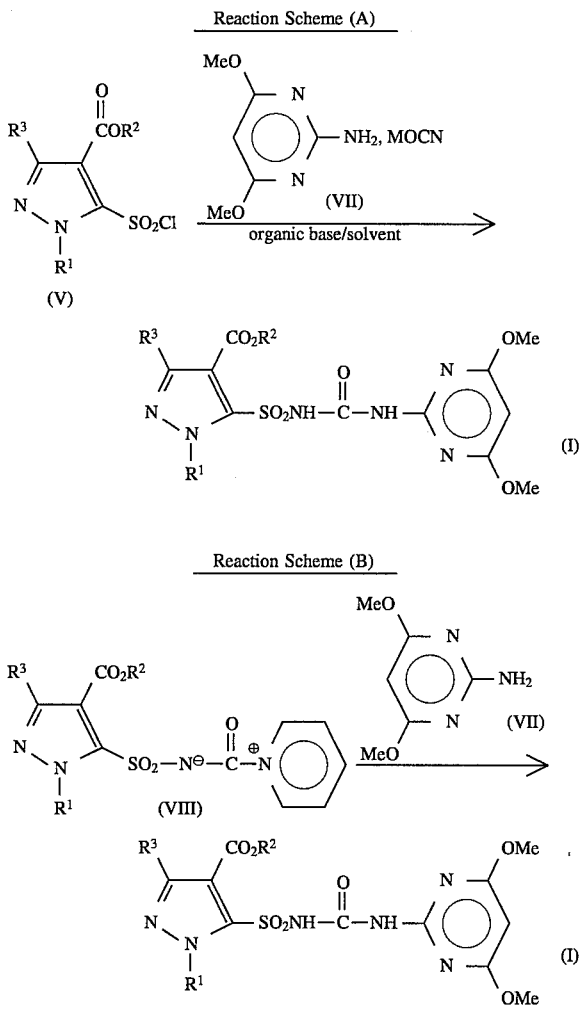

In the above reaction schemes, $R^1$, $R^2$ and $R^3$ are as defined above, and

M represents a monovalent metal atom.

The method (A) according to the present invention is carried out by reacting sulfonylchloride of formula (V) with 2-amino-4,6-dimethoxypyrimidine of formula (VII) in the presence of a metal cyanate and an organic base catalyst.

Since the reaction of the method (A) according to the present invention is carried out in a stoichiometric manner, the starting material and the reactant can be reacted together in the equimolar amounts. However, considering the reaction efficiency, it is preferable that each of sulfonylchloride of formula (V) and the metal cyanate is used in the ratio of 1.0 to 2.0 equivalent weights with respect to the amine compound of formula (VII). Further, in view of the fact that the compound of formula (V) is relatively expensive it is preferable to use the compound of formula (V) in the ratio of 1.0 to 1.2 equivalent weights with respect to the amine compound (VII).

Metal cyanate which can be used in this reaction includes a monovalent alkali metal cyanate, preferably sodium cyanate or potassium cyanate.

The organic base which can be used as a catalyst in the method (A) of the present invention is the most important factor which can determine the reaction rate and the reaction selectivity and includes, for example, tertiary alkylamine, pyridine derivative or cyclic tertiary amine. Particularly, when pyridine or triethylamine is used as the catalyst, the best result can be provided in view of the reaction selectivity and yield. The reaction result becomes better as the used amount of the organic base is increased in the range of 0.01 to 2.0 equivalent weight with respect to the amine of formula (VII). However, considering the economical view, it is preferable that the organic base is used in the ratio of 0.1 to 1.0 equivalent weight with respect to the amine compound of formula (VII).

The solvent which can be used in this reaction (A) may be a single solvent selected from the group consisting of halogenated hydrocarbons and aromatic hydrocarbons such as dichloromethane, trichloromethane, 1,2-dichloroethane, etc., aprotic polar solvents such as dimethylformamide, dimethylsulfoxide, etc., ethers such as ethyl ether, tetrahydrofuran, dioxane, etc., nitriles such as acetonitrile, propionitrile, etc., ketones such as acetone, methylethyl ketone, diisopropyl ketone, etc., and the like, or a mixture of two or more solvents selected therefrom. In this case, the solvent is preferably used under anhydrous condition where it is possible.

Although the reaction temperature can be varied within a relatively broad range, the reaction may preferably be carried out at 0° C. to the refluxing temperature of the solvent used therein. When considering the reaction rate, the production of by-products and the like, it is particularly preferable that the reaction is carried out at 25° to 45° C. In this case, the reaction generally takes 0.5 to 4.0 hours.

When sulfonylchloride of formula (V) is reacted with metal cyanate and the amine compound of formula (VII) according to the method (A) under such a special reaction condition, the desired sulfonylurea derivative of formula (I) can be obtained in a high yield of 88% or more and in a high purity without production of by-product.

Sulfonylchloride of formula (V) which is used as the starting compound in the method (A) for preparing the sulfonylurea derivative of formula (I) according to the present invention is a compound known as an intermediate compound useful for preparation of the sulfonylurea-based herbicide. European Early Published Patent No. 87,780 as mentioned above also describes the method for preparing the intermediate compound of formula (V), in which a compound of formula (IX) is reacted with chlorine gas to prepare the pyrazole sulfonylchloride compound of formula (V), as depicted in the following reaction scheme:

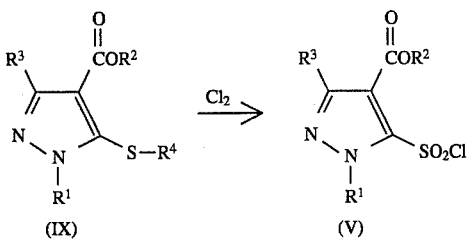

wherein

R¹, R² and R³ are as defined above, and

R⁴ represents hydrogen or benzyl.

However, since such known method uses chlorine gas which is highly poisonous to humans, the reaction should be practiced by means of a special safety apparatus. Further, this method has a disadvantage in that the by-product such as the compound of the following general formula (X):

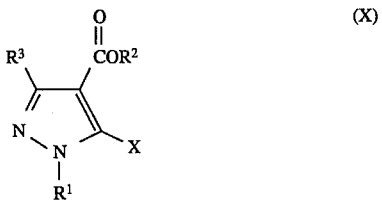

wherein R¹, R² and R³ are as defined above and X represents hydrogen or Cl, may be produced in a substantial amount due to the excessive strong reactivity of chlorine gas.

The present invention establishes a method in which aqueous hydrochloric acid solution and hydrogen peroxide solution which are easy to handle and can be readily controlled in their reactivities are used in place of chlorine gas, and therefore the problems involved in the known method above can be solved. Specifically, according to the present invention the pyrazole sulfonylchloride derivative of formula (V) can be simply prepared by reacting a pyrazole disulfide derivative of formula (XI) with aqueous hydrochloric acid solution and hydrogen peroxide solution as depicted in the following reaction scheme:

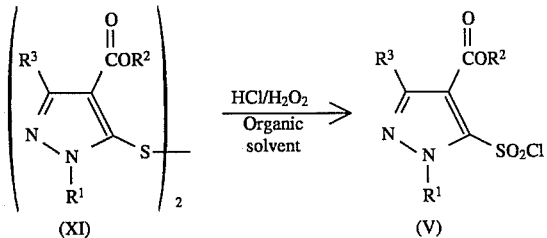

wherein R¹, R² and R³ are as defined above.

The process for preparing the compound of formula (V) as defined above is a novel method which was never described in prior art up to the present and therefore is another object of the present invention.

According to the process for preparing the compound of formula (V) of the present invention, the reaction can be carried out either by reacting together the starting compound and the reactant each of which is dissolved in a separate solvent or by dissolving the starting compounds directly in aqueous hydrochloric acid solution without any solvent. When the reaction is carried out using the solvent, the solvent which can preferably be used may be an organic solvent, for example, optionally halogenated alkane solvents such as n-hexane, dichloromethane, etc, toluene and the like.

In this reaction, aqueous hydrochloric acid solution and hydrogen peroxide solution can be used in the ratio of 2.0 equivalent weights or more with respect to the starting disulfide compound of formula (XI) without any special limitation. However, in view of the fact that the production of by-products should be minimized, the reaction time should be shortened and the teaction efficiency should be increased, it is preferable that they are used in the ratio of 6.0 to 8.0 equivalent weights, respectively, with respect to the disulfide compound (XI).

In addition, the reaction time of this reaction according to the present invention is prolonged in the case of the inner temperature of the reaction vessel below 20° C. whereas the yield of the desired compound of formula (V) may be decreased at the temperature above 50° C. due to hydrolysis of the compound of formula (V). Accordingly, the reactants should be carefully introduced so that the inner temperature of the reaction vessel can be maintained in the range of 30° to 50° C., more preferably 35° to 45° C.

The disulfide compound of formula (XI) which can be used as the starting compound in the process for preparing the compound of formula (V) according to the present invention is a known compound and can be prepared, for example, by reacting a dithiocarbazate derivative of formula (XII) with a base and then oxidizing the reaction product in a conventional manner according to the method described in Korean Patent Application No. 92-24734 which belongs to the present inventors, as depicted in the following reaction scheme:

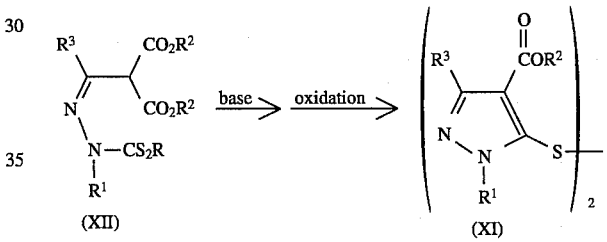

wherein

R¹, R² and R³ are as defined above, and

R represents $C_1-C_4$ alkyl, $C_2-C_4$ alkenyl, aralkyl(preferably benzyl) or aryl(preferably phenyl).

In addition, the method (B) according to the present invention prepares a sulfonylurea derivative of formula (I) by reacting 1-[[(pyrazolesulfonyl)amino]carbonyl]pyridinium hydroxide of formula (VIII) with 2-amino-4,6-dimethoxypyrimidine of formula (VII).

Since the reaction of the method (B) according to the present invention is carried out in a stoichiometric manner, the starting material of formula (VIII) and the amine derivative of formula (VII) can be reacted together in the approximately equimolar amounts. However, the amine derivative of formula (VII) can be used in a somewhat excessive amount.

The solvent which can be used in the reaction (B) may be a single solvent selected from the group consisting of halogenated hydrocarbons and aromatic hydrocarbons such as dichloromethane, trichloromethane, 1,2-dichloroethane, etc., aprotic polar solvents such as dimethylformamide, dimethylsulfoxide, etc., ethers such as ethyl ether, tetrahydrofuran, dioxane, etc, nitriles such as acetonitrile, propionitrile, etc., ketones such as acetone, methylethyl ketone, diisopropyl ketone, etc., and the like, or a mixture of two or more solvents selected therefrom. In this case, the solvent is preferably used under anhydrous condition where it is possible.

Although the reaction temperature can be varied within a relatively broad range, the reaction may preferably be carried out at 0° C. to the refluxing temperature of the solvent used therein. When considering the reaction rate, the production of by-products and the like, it is particularly preferable that the reaction can be carried out at 25° to 45° C. In this case, the reaction generally takes 0.5 to 4.0 hours.

When 1-[[(pyrazolesulfonyl)amino]carbonyl]pyridinium hydroxide inner salt of formula (VIII) is reacted with the amine derivative of formula (VII) according to the method (B) under such a special reaction condition, the desired sulfonylurea derivative of formula (I) can be obtained in a high yield of 95% or more and in a high purity without production of by product.

The starting compound 1-[[(pyrazolesulfonyl)amino]carbonyl]pyridinium hydroxide inner salt of formula (VIII) used in the method (B) according to the present invention is a novel compound which was never described in any prior publications before the present invention. Accordingly, the compound of formula (VIII) constitutes another object of the present invention. Specifically, the present invention relates to a novel 1-[[(pyrazolesulfonyl)amino]carbonyl]pyridinium hydroxide inner salt of formula (VIII):

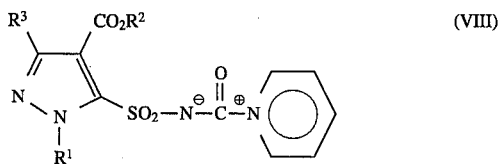

wherein $R^1$, $R^2$ and $R^3$ are as defined above, and to a process for preparing thereof.

In the compound of formula (VIII) above, $R^1$ and $R^2$ may be a straight or branched $C_1$–$C_4$ alkyl and preferably a straight alkyl, for example, methyl, ethyl, n-propyl, n-butyl, etc,. More preferably, $R^1$ and $R^2$ represent methyl or ethyl. The most preferable compound of formula (VIII) is a compound wherein $R^1$ represents methyl, $R^2$ represents ethyl and $R^3$ represents hydrogen.

In addition, the present invention provides a process for preparing the novel compound of formula (VIII) above. According to the process of the present invention, the compound of formula (VIII) can be prepared by reacting a sulfonylchloride compound of formula (V):

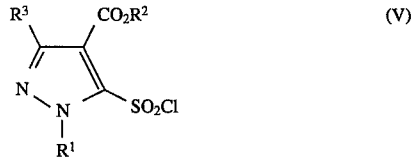

wherein $R^1$, $R^2$ and $R^3$ are as defined above, with an alkali metal cyanate and pyridine in the presence of a solvent.

Since the above reaction according to the present invention is carried out in a stoichiometric manner, the starting material and the reactant can be reacted together in the equimolar amounts. However, considering the reaction efficiency, it is preferable that each of sulfonylchloride of formula (V) and alkali metal cyanate is used in the ratio of 1.0 to 2.0 equivalent weights with respect to the amine compound of formula (VII). Further, in view of the fact that pyridine is relatively expensive it is preferable to use pyridine in the ratio of 1.0 to 1.2 equivalent weights.

As the alkali metal cyanate which can be used in this reaction, although both sodium cyanate and potassium cyanate can preferably used, the use of sodium cyanate is particularly preferable.

The solvent which can be used in this reaction may be a single solvent selected from the group consisting of halogenated hydrocarbons such as dichloromethane, trichloromethane, 1,2-dichloroethane, etc., ethers such as ethyl ether, tetrahydrofuran, dioxane, etc., nitriles such as acetonitrile, propionitrile, etc., ketones such as acetone, methylethyl ketone, diisopropyl ketone, etc., and the like, or a mixture of two or more solvents selected therefrom. Among those solvents, dichloromethane, tetrahydrofurane, dioxane, acetonitrile and the like, particularly acetonitrile is preferably used. In this case, the solvent is preferably used under anhydrous condition where it is possible.

Although the reaction temperature can be varied within a relatively broad range, the reaction may preferably be carried out at 0° C. to the refluxing temperature of the solvent used therein. When considering the reaction rate, the production of by-products and the like, it is particularly preferable that the reaction can be carried out at 35° to 45° C. In this case, the reaction generally takes 0.5 to 4.0 hours.

Since the compound of formula (VIII) prepared according to the method of the present invention has a very high reactivity and is unstable and therefore can be easily converted into an amide compound by the reaction with atmospheric moisture when the compound (VIII) is exposed to air, it is preferable that the compound of formula (VIII) is stored under nitrogen atmosphere. However, when the compound of formula (VIII) is used in preparation of the compound of formula (I) according to the present invention, it may be reacted in situ with the amine derivative of formula (VII) without isolation from the reaction mixture.

The sulfonylchloride compound of formula (V) which is used as the starting compound in the reaction for preparing the compound of formula (VIII) above according to the present invention can be prepared according to the following method as explained in the method for preparation of sulfonylchloride compound of formula (V) which is the starting compound in the method (A) above:

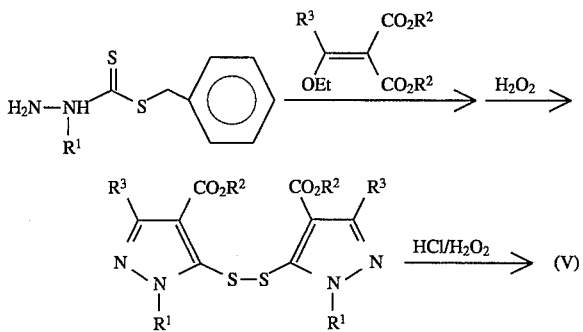

wherein $R^1$, $R^2$ and $R^3$ are as defined above.

The present invention will be more specifically illustrated by the following examples. However, it should be understood that the present invention is not limited by these examples in any manner.

EXAMPLE 1

Preparation of bis(4-ethoxycarbonyl-1-methylpyrazole)-5-disulfide 2.12 g (10.0 mmole) of benzyl 2-methyldithiocarbazate and 2.25 g (10.2 mmole) were mixed with 2.40 g of anhydrous ethanol and the mixture was heated to dissolve all the substances. To this heated mixture was added 3.89 g of 21% sodium ethoxide and the mixture was refluxed for 8 hours and then distilled in vacuo to remove the solvent. The residue was dissolved in 2.50 g of dichloromethane and 3.00 g of water. The aqueous layer was adjusted to pH 7 with 20% sulfuric acid and 0.48 g of 35% aqueous hydrogen peroxide solution was added thereto over one hour at room temperature. The reaction mixture was continuously stirred for further one hour at room temperature and allowed to separate the layers. The separated organic layer was dried over anhydrous magnesium sulfate and distilled in vacuo to remove the solvent to obtain 1.70 g of the title compound (Yield 92%, Purity 98%).

EXAMPLE 2

Preparation of 4-ethoxycarbonyl-1-methylpyrazole-5-sulfonylchloride 1.67 g (4.5 mmole) of the disulfide compound prepared in Example 1 was added to 3.75 g (36.0 mmole) of 35% aqueous hydrochloric acid solution and 2.00 g of dichloromethane at room temperature and the reaction mixture was warmed to 40° C. and then maintained for 30 minutes at the same temperature. To this mixture was added 2.62 g (27.0 mmole) of 35% aqueous hydrogen peroxide solution at 40° to 45° C. over one hour and the whole mixture was continuously stirred for further one hour and then allowed to separate the layers. The separated organic layer was dried over anhydrous magnesium sulfate and the solvent was removed therefrom to obtain 2.16 g of the title compound (Yield 95%, Purity 95%).

EXAMPLE 3

Preparation of 4-ethoxycarbonyl-1-methyl-5-pyrazole disulfide 30.6 g of methyl 3-[2', 2'-(diethoxycarbonyl)ethylidene]-2-methyldithiocarbazate and 8 g of sodium ethoxide were added to 250 ml of absolute ethanol and the mixture was heated under reflux in the nitrogen atmosphere for about 10 hours. When the reaction was completed, ethanol was distilled off and 200 ml of water and 500 ml of methylene dichloride were added to the residue. The mixture was adjusted to approximately pH 8 with 98% sulfuric acid to separate the layers. The aqueous layer was collected and then adjusted to pH 2. The resulting product was extracted with 500 ml of methylene dichloride. 5.0 g of 38% hydrogen peroxide was added to the methylene dichloride layer and the mixture was stirred for 3 hours at room temperature to complete the reaction. The reaction mixture was allowed to separate the layers and the organic layer was collected, dried over anhydrous magnesium sulfate and then distilled in vacuo to remove the solvent to obtain 16.8 g of the title compound as brown solid (Yield 91%, Purity 98%).

EXAMPLE 4

Preparation of 4-ethoxycarbonyl-1-methylpyrazole-5-sulfonylchloride 370 g of 4-ethoxycarbonyl-1-methyl-5-pyrazole disulfide, 390 g of dichloromethane and 834 g of 35% aqueous hydrochloric acid solution were introduced into a reaction flask. The reaction mixture was stirred at room temperature to dissolve the starting material and then 560 g of 36% hydrogen peroxide was slowly added dropwise thereto over 2 hours during which the inner temperature of the flask should be maintained at approximately 40° C. After the addition of hydrogen peroxide was completed, the reaction mixture was stirred for further 30 minutes while maintaining the same temperature to complete the reaction, cooled to room temperature and then allowed to separate the layers. The separated organic layer was dried over anhydrous magnesium sulfate and the solvent was then removed therefrom to obtain 476 g (Yield 94%) of the title compound as yellow liquid substance (Purity 94% as measured by gas chromatography).

EXAMPLE 5

Preparation of 1-[[(4-ethoxycarbonyl-1-methylpyrazole-5-sulfonyl)amino]carbonyl]pyridinium hydroxide inner salt 1.08 g (16.6 mmole) of anhydrous sodium cyanate, 1.25 g (15.8 mmole) of dry pyridine and 20.0 g of dry acetonitrile were mixed together and the resulting mixture was then stirred under nitrogen atmosphere while maintaining the temperature of 40° C. To this mixture was added 3.80 g (15.0 mmole) of 4-ethoxycarbonyl-1-methylpyrazole-5-sulfonylchloride over one hour. The reaction mixture was then stirred for further 2 hours while maintaining the temperature of 40° to 45° C. to complete the reaction. After the reaction was completed, the reaction solution was filtered under nitrogen atmosphere. The solvent and the remaining pyridine were removed from the filtrate at normal temperature by means of a vacuum pump to obtain the crude product which was then washed with 10.00 g of dry ethyl ether and dried to obtain 4.68 g (Yield 92%) of the title compound as the white solid.

$^1$H NMR (CDCl$_3$): δ9.38(2H), 8.30(1H), 7.85(1H), 7.82(2H), 4.34(3H, CH$_3$—N<), 4.25(2H, OCH$_2$—), 1.30(3H, C—CH$_3$)

IR (cm$^{-1}$): 3120, 3075, 2986, 1717

EXAMPLE 6

Preparation of 1-[[(4-ethoxycarbonyl-1-methylpyrazole-5-sulfonyl)amino]carbonyl]pyridinium hydroxide inner salt 2.53 g (10 mmole) of 4-ethoxycarbonyl-1-methylpyrazole-5-sulfonylchloride was dissolved in 10.00 g of anhydrous acetonitrile. To the resulting solution was added dropwise 0.83 g (10.5 mmole) of dry pyridine over 5 minutes under nitrogen atmosphere by means of a syringe and the mixture was maintained at 40° C. To this mixture was added 0.72 g (11.0 mmole) of anhydrous sodium cyanate and the mixture was stirred while maintaining the temperature of 40° to 45° C. to complete the reaction. Then, the reaction mixture was treated according to the same procedure as Example 5 to obtain 3.50 g (Yield 90%) of the title compound as the white solid substance.

$^1$H NMR (CDCl$_3$): δ9.39(2H), 8.30(1H), 7.85(1H), 7.83(2H), 4.34(3H, CH$_3$—N<), 4.25(2H, OCH$_2$—), 1.30(3H, C—CH$_3$)

IR (cm$^{-1}$): 3120, 3075, 2986, 1717

EXAMPLE 7

Preparation of
N-[[4,6-dimethoxypyrimidin-2-yl)aminocarbonyl]-
4-ethoxycarbonyl-1-methylpyrazole-5-sulfonamide 7.27 g of anhydrous sodium cyanate, 15.78 g of 2-amino-4,6-dimethoxypyrimidine, 8.04 g of pyridine and 40 g of dry acetonitrile were mixed together and the mixture was warmed to 45° C. under nitrogen atmosphere. To this mixture was added 28.46 g of 1-methyl-4-ethoxycarbonylpyrazole-5-sulfonylchloride over 2 hours and the reaction mixture was stirred for further 2 hours while maintaining the temperature of 45° C. After the completion of the reaction was identified by liquid chromatography, the reaction product was extracted with 200 g of dichloromethane and 40 g of 5% aqueous sulfuric acid solution. The extracted organic layer was dried over anhydrous magnesium sulfate and then filtered. The organic solvent was removed from the product to obtain 41.30 g (Yield 98%) of the title compound as a solid state.

EXAMPLE 8

Preparation of
N-[(4,6-dimethoxypyrimidin-2-yl)aminocarbonyl]-
4-ethoxycarbonyl-1-methylpyrazole-5-sulfonamide 2.603 g of 4-ethoxycarbonyl-1-methylpyrazole-5-sulfonylchloride was dissolved in 20.0 ml of acetonitrile. To the resulting solution were added 0.715 g of sodium cyanate and 1.552 g (10.0 mM) of 4,6-dimethoxy-2-aminopyrimidine with stirring. The reaction mixture was maintained at 40° C. for about 10 minutes and then 0.396 g of pyridine was added dropwise thereto over 5 minutes via a syringe. While maintaining the temperature of 40° to 45° C., the reaction mixture was continuously and vigorously stirred for 3 hours to complete the reaction. After the reaction was completed, the reaction mixture was adjusted to pH 4 by adding 5% aqueous sulfuric acid solution and dichloromethane to extract the reaction product. The extracted organic layer was dried over anhydrous magnesium sulfate and then filtered. The organic solvent was removed from the filtrate to obtain 4.103 g (Yield 99%) of the title compound in the solid state.

EXAMPLE 9 TO 15

According to the same procedure as Example 7, 2.603 g of 4-ethoxycarbonyl-1-methylpyrazole-5-sulfonylchloride was reacted with 1.552 g (10.0 mM) of 2-amino-4,6-dimethoxypyrimidine under the reaction conditions as shown in the following table to obtain the same desired compound as in Example 7. The results obtained in these examples are described in the following table.

| Example No. | Metal cyanate (Equi.)*[1] | Catalyst (Equi.) | Solvent (20.0 ml) | Reaction Temp. (°C.) | Reaction Time (hr) | Yield *[2] |
|---|---|---|---|---|---|---|
| 9 | NaOCN (1:1) | pyridine (0.5) | $CH_3CN$ | 25 | 12 | 95 |
| 10 | NaOCN (1:1) | pyridine (0.5) | $CH_3CN$ | reflux | 0.5 | 97 |
| 11 | NaOCN (1:1) | pyridine (0.5) | $CH_2Cl_2$ | reflux | 5 | 90 |
| 12 | KOCN (1:1) | pyridine (0.5) | $CH_3CN$ | 40 | 2 | 98 |
| 13 | KOCN (1:1) | pyridine (0.5) | $CH_2Cl_2$ | reflux | 5 | 88 |
| 14*[3] | NaOCN | Not used | $CH_3CN$ | 25 | 12 | 42 |
| 15*[3] | NaOCN | TBAB*[4] (0.1) | $CH_3CN$ | 25 | 12 | 50 |

Note:
*[1]Equivalent weight (Equi.) is based on 4,6-dimethoxy-2-aminopyridine (10.0 mM).
*[2]Yield is determined by separation of the desired product with column chromatography.
*[3]Examples 14 and 15 are the comparative examples in which the catalyst is not used or the conventional catalyst TBAB is used
*[4]TBAB = tetra n-butylammonium bromide

EXAMPLE 16

Preparation of N-[(4-methoxy-6-methylpyrimidin-2-yl)aminocarbonyl]-1-methylpyrazole-5-sulfonamide 23.8 g of 4-methoxycarbonyl-1-methylpyrazole-5-sulfonamide was dissolved in 100 g of acetonitrile and 8.0 g of sodium cyanate and 13.9 g of 2-amino-4-methoxy-6-methylpyrimidine were added thereto with stirring. The reaction mixture was maintained at 40° C. for about 10 minutes. To this mixture was added dropwise 0.3 g of pyridine over 5 minutes. The whole mixture was vigorously and continuously stirred for 2 hours while maintaining the temperature of 40° to 45° C. to complete the reaction. The mixture was then treated according to the same procedure as Example 7 to obtain 35.3 g (Yield 92%) of the title compound.

EXAMPLE 17

Preparation of
N-(4-methoxy-6-methyl-1,3,5-triazin-2
-yl)aminocarbonyl]-1,3-dimethyl-5-
methoxycarbonylpyrazole-4-sulfonamide 25.2 g of 1,3-dimethyl-5-methoxycarbonylpyrazole-4-sulfonylchloride, 13.9 g of 2-amino-4-methoxy-6-methyl-1,3,5-triazine, 9.7 g of potassium cyanate and 0.3 g of pyridine were dissolved 100 ml of acetonitrile and the mixture was allowed to react for 2 hours at 50° C. The reaction mixture was then treated according to the same procedure as Example 7 to obtain 35.5 g (Yield 89%) of the title compound.

EXAMPLE 18

Preparation of
N-[(4,6-dimethoxypyrimidin-2-yl)aminocarbonyl]-
4-ethoxycarbonyl-1-methylpyrazole-5-sulfonamide 3.42 g (10.1 mmole) of 1-[[(4-ethoxycarbonyl-1-methylpyrazole-5-sulfonyl)amino]carbonyl]pyridinium hydroxide was dissolved in 10.00 g of dry acetonitrile. To the resulting solution was added 1.55 g (10.0 mmole) of 2-amino-4,6-dimethoxypyrimidine with stirring. The reaction mixture was stirred for one hour while maintaining the temperature of 40° to 45° C. to complete the reaction. After the reaction was completed, 25.00 g of water was added to the reaction solution. The mixture was then adjusted to pH 5 to 6, cooled to 25° C. and filtered. The resulting product was washed with water and acetonitrile and then dried to obtain 4.10 g (Yield 99%) of the title compound as the white powder.

The more pertinent important features of the present invention have been outlined above in order that the detailed description of the invention which follows will be better understood and that the present contribution to the art can be fully appreciated. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

What is claimed is:

1. A compound 1-[[(pyrazolesulfonyl)amino]carbonyl]pyridinium hydroxide having the following formula (VIII),

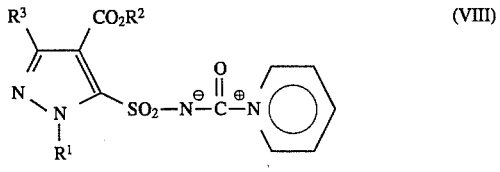

wherein
$R^1$ represents hydrogen, $C_1$–$C_4$ alkyl or phenyl,
$R^2$ represents hydrogen, $C_1$–$C_4$ alkyl, allyl or propargyl, and
$R^3$ represents hydrogen, methyl, ethyl or phenyl.

2. The compound of formula (VIII) according to claim 1, characterized in that $R^1$ represents methyl, $R^2$ represents ethyl and $R^3$ represents hydrogen.

3. A process for preparing sulfonylchloride derivatives having the following formula (V),

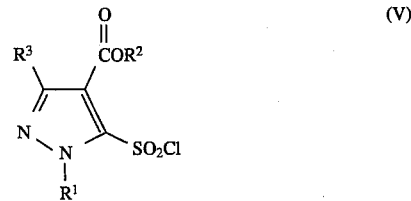

wherein
$R^1$ represents hydrogen, $C_1$–$C_4$ alkyl or phenyl;
$R^2$ represents hydrogen, $C_1$–$C_4$ alkyl, allyl or propargyl; and
$R^3$ represents hydrogen, methyl, ethyl or phenyl, comprising reacting a pyrazole disulfide derivative of formula (XI),

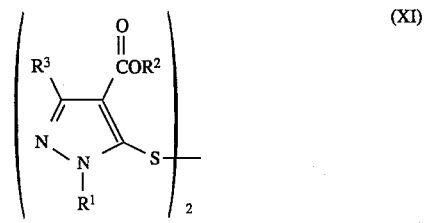

wherein $R^1$, $R^2$ and $R^3$ are as defined above, with an aqueous hydrochloric acid solution and hydrogen peroxide solution in the presence of an organic solvent.

4. The process according to claim 3, wherein said solvent is n-hexane; dichloromethane or toluene.

5. The process according to claim 3, wherein aqueous hydrochloric acid solution and hydrogen peroxide solution are used in an amount of 6.0 to 8.0 equivalent weights, respectively, with respect to the disulfide compound of formula (XI).

6. The process according to any one of claims 3 to 5, wherein the reaction temperature is 35° to 45° C.

* * * * *

UNITED STATES PATENT AND TRADEMARK OFFICE
CERTIFICATE OF CORRECTION

PATENT NO. : 5,534,637

DATED : July 9, 1996

INVENTOR(S) : Jong Kwon Choi et al.

It is certified that error appears in the above-identified patent and that said Letters Patent is hereby corrected as shown below:

On the title page, item [54] and column 1, line 1, change PREPARTION" to --PREPARATION--.

IN THE TITLE:

Signed and Sealed this

Twenty-fourth Day of December, 1996

Attest:

BRUCE LEHMAN

*Attesting Officer*     *Commissioner of Patents and Trademarks*